United States Patent
Clark et al.

(10) Patent No.: US 10,478,613 B2
(45) Date of Patent: *Nov. 19, 2019

(54) TEMPORARY IMPLANTABLE MEDICAL ELECTRICAL STIMULATION LEAD

(71) Applicant: Cardiac Pacemakers, Inc., St. Paul, MN (US)

(72) Inventors: Bryan A. Clark, Forest Lake, MN (US); Timothy R. Jackson, Minneapolis, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/371,137

(22) Filed: Dec. 6, 2016

(65) Prior Publication Data

US 2017/0080209 A1 Mar. 23, 2017

Related U.S. Application Data

(63) Continuation of application No. 13/937,850, filed on Jul. 9, 2013, now Pat. No. 9,545,207.

(Continued)

(51) Int. Cl.
*A61N 1/05* (2006.01)
*A61B 5/04* (2006.01)

(52) U.S. Cl.
CPC .......... *A61N 1/05* (2013.01); *A61B 5/04001* (2013.01); *A61N 1/0551* (2013.01); *A61N 1/0558* (2013.01)

(58) Field of Classification Search
CPC ...... A61N 1/05; A61N 1/0551; A61N 1/0558; A61B 5/04001

(Continued)

(56) References Cited

U.S. PATENT DOCUMENTS

| 5,042,143 A | 8/1991 | Holleman et al. |
| 5,861,023 A | 1/1999 | Vachon |

(Continued)

FOREIGN PATENT DOCUMENTS

| JP | 2006517838 A | 8/2006 |
| WO | 2011037978 A2 | 3/2011 |

OTHER PUBLICATIONS

International Preliminary Report on Patenability issued in PCT/US2013/060483, completed Jan. 7, 2015, 10 pages.

(Continued)

*Primary Examiner* — Christopher Koharski
*Assistant Examiner* — Pamela M. Bays
(74) *Attorney, Agent, or Firm* — Faegre Baker Daniels, LLP

(57) ABSTRACT

A temporary implantable medical device lead includes a connector, a helically coiled conductor and a first mechanical element. The connector is configured to connect the lead to an external control module. The helically coiled conductor has a proximal end mechanically and electrically connected to the connector. The conductor includes a plurality of filars mechanically and electrically connected to the connector. The first mechanical element includes a metal tube having a plurality of longitudinally spaced grooves formed along an exterior of the tube. The plurality of longitudinally spaced grooves receives at least some of the plurality of filars. The at least some of the plurality of filars electrically connected to the first mechanical element such that the first mechanical element is configured as an electrode to deliver electrical stimulation to portions or systems of a body from the external control module.

20 Claims, 5 Drawing Sheets

Related U.S. Application Data

(60) Provisional application No. 61/675,407, filed on Jul. 25, 2012.

(58) Field of Classification Search
USPC .................................................. 607/115–118
See application file for complete search history.

(56) References Cited

U.S. PATENT DOCUMENTS

| | | |
|---|---|---|
| 6,104,960 A | 8/2000 | Duysens et al. |
| 6,129,751 A | 10/2000 | Lucchesi et al. |
| 7,881,783 B2 | 2/2011 | Bonde et al. |
| 2001/0044646 A1 | 11/2001 | Marshall et al. |
| 2003/0088301 A1 | 5/2003 | King |
| 2004/0088034 A1 | 5/2004 | Smits et al. |
| 2004/0162600 A1* | 8/2004 | Williams ................ A61N 1/05 607/122 |
| 2005/0080471 A1 | 4/2005 | Chitre et al. |
| 2005/0222659 A1 | 10/2005 | Olsen et al. |
| 2007/0179582 A1 | 8/2007 | Marshall et al. |
| 2007/0250143 A1 | 10/2007 | Sommer |
| 2007/0255366 A1 | 11/2007 | Gerber et al. |
| 2007/0255369 A1 | 11/2007 | Bonde et al. |
| 2007/0255370 A1 | 11/2007 | Bonde et al. |
| 2007/0255371 A1 | 11/2007 | Bonde et al. |
| 2010/0268310 A1* | 10/2010 | Bonde ................ A61N 1/0558 607/116 |
| 2011/0071608 A1 | 3/2011 | Fleischhacker et al. |
| 2011/0238146 A1 | 9/2011 | Wedan et al. |
| 2011/0257500 A1 | 10/2011 | Wells et al. |
| 2012/0184836 A1* | 7/2012 | Kolberg ................ A61N 1/05 600/373 |

OTHER PUBLICATIONS

International Search Report and Written Opinion issued in PCT/US2013/049721, dated Mar. 4, 2014, 11 pages.
International Search Report and Written Opinion issued in PCT/US2013/060483, dated Feb. 17, 2014.
Partial International Search Report (from invitation to Pay Additional Fees) issued in PCT/US2013/060483, dated Nov. 22, 2013.
Second Written Opinion issued in PCT/US2013/060483 dated Aug. 25, 2014, 6 pages.

* cited by examiner

TEMPORARY IMPLANTABLE MEDICAL ELECTRICAL STIMULATION LEAD

CROSS-REFERENCE TO RELATED APPLICATION

This application is a continuation of U.S. application Ser. No. 13/937,850 filed Jul. 9, 2013, now U.S. Pat. No. 9,545,207 which claims the benefit under 35 U.S.C. section 119(e) to U.S. Provisional Application 61/675,407, filed Jul. 25, 2012, all of which are herein incorporated by reference in their entirety

TECHNICAL FIELD

The present disclosure relates to implantable medical leads. More particularly, the present disclosure relates to temporary implantable medical leads including a plurality of electrodes.

BACKGROUND

Temporary implantable medical leads may be used to evaluate the efficacy of stimulation (e.g., neurostimulation) prior to implanting chronically implantable systems within a patient. For example, as a treatment for urinary incontinence, patients may be implanted with a trial percutaneous nerve evaluation (PNE) lead to evaluate the efficacy of sacral nerve stimulation.

Temporary leads that incorporate only one electrode (i.e., unipolar) are used in conjunction with a ground pad. The ground pad is applied to the patient's skin and connected to the electrical stimulation element to complete the electrical circuit. The ground pad may cause the patient discomfort, and can become dislodged or disconnected during the test period, thus preventing test stimulation therapy from occurring. In addition, the temporary lead may migrate, potentially causing the unipolar lead to lose the ability to deliver effective therapy. As a result, higher non-responder rates can occur in patients receiving the temporary lead compared to patients receiving a permanent pacing lead to evaluate the efficacy of stimulation.

SUMMARY

Disclosed herein are various embodiments of a temporary implantable medical device lead including multiple stimulation electrodes, as well as medical device systems including such temporary implantable medical device leads.

In Example 1, a temporary implantable medical device lead includes a connector configured to connect the lead to an external control module. A helically coiled conductor has a proximal end mechanically and electrically connected to the connector. The conductor includes a plurality of insulated filars. An insulative layer is removed from an uninsulated portion of each of the filars near a distal end of the conductor. The uninsulated portion of each of the filars is exposed at an outer surface of the conductor such that the exposed uninsulated portions of the filars define a plurality of electrodes at longitudinally spaced sections near the distal end of the conductor.

In Example 2, the temporary implantable medical device lead according to Example 1, wherein a first electrode is defined by the uninsulated portion of at least one of the plurality of filars and a second electrode is defined by the uninsulated portions of at least one other of the plurality of filars.

In Example 3, the temporary implantable medical device lead according to either Example 1 or Example 2, and further comprising a conductive mechanical element including one or more grooves that electrically couple with the uninsulated portion of at least one filar.

In Example 4, the temporary implantable medical device lead according to Example 3, wherein one or more grooves have a depth approximately equal to a diameter of the retained at least one filar.

In Example 5, the temporary implantable medical device lead according to any of Examples 1-4, and further comprising one or more conductive elements wound co-radially with and electrically coupled to the uninsulated portion of at least one filar of the conductor, wherein the one or more conductive elements are not mechanically connected to the connector at the proximal end.

In Example 6, the temporary implantable medical device lead according to Example 5, wherein the one or more conductive elements comprises one or more additional filars.

In Example 7, the temporary implantable medical device lead according to Example 5, wherein the one or more conductive elements comprises a ribbon conductor.

In Example 8, the temporary implantable medical device lead according to any of Examples 1-7, wherein the plurality of filars are wound in alternating multi-turn segments, and wherein one or more multi-turn segments for each filar are exposed at the outer surface of the conductor to define the plurality of electrodes.

In Example 9, a system includes an externally carried control module and a temporary implantable medical device lead. The temporary implantable medical device lead includes a connector configured to connect the lead to the control module. A helically coiled conductor includes proximal end mechanically and electrically connected to the connector. The conductor includes a plurality of insulated filars. An insulative layer is removed from an uninsulated portion of each of the filars near a distal end of the conductor. The uninsulated portion of each of the filars is exposed at an outer surface of the conductor such that the exposed uninsulated portions of the filars define a plurality of electrodes at longitudinally spaced sections near the distal end of the conductor. During stimulation, the control module is configured to operate a first of the plurality of electrodes as a cathode and a second of the plurality of electrodes as an anode.

In Example 10, the system according to Example 9, wherein a first electrode is defined by the uninsulated portion of at least one of the plurality of filars and a second electrode is defined by the uninsulated portions of at least one other of the plurality of filars.

In Example 11, the system according to either Example 9 or Example 10, and further comprising a conductive mechanical element including one or more grooves that electrically couple with the uninsulated portion of at least one filar.

In Example 12, the system according to Example 11, wherein one or more grooves have a depth approximately equal to a diameter of the retained at least one filar.

In Example 13, the system according to any of Examples 9-12, and further comprising one or more conductive elements wound co-radially with and electrically coupled to the uninsulated portion of at least one filar of the conductor, wherein the one or more conductive elements are not mechanically connected to the connector at the proximal end.

In Example 14, the system according to Example 13, wherein the one or more conductive elements comprises one or more additional filars.

In Example 15, the system according to Example 13, wherein the one or more conductive elements comprises a ribbon conductor.

In Example 16, the system according to any of Examples 9-15, wherein the plurality of filars are wound in alternating multi-turn segments, and wherein one or more multi-turn segments for each filar are exposed at the outer surface of the conductor to define the plurality of electrodes.

In Example 17, a temporary implantable medical device lead includes a connector configured to connect the lead to an externally carried control module, and a lead body including a helically coiled conductor having a proximal end mechanically and electrically connected to the connector. The conductor includes a plurality of insulated filars. An insulative layer is removed from an uninsulated portion of each of the filars near a distal end of the conductor. The uninsulated portion of each of the filars is exposed at an outer surface of the lead body such that the exposed uninsulated portions of the filars define a plurality of electrodes at longitudinally spaced sections.

In Example 18, the temporary implantable medical device lead according to Example 17, wherein a first electrode is defined by the uninsulated portion of at least one of the plurality of filars and a second electrode is defined by the uninsulated portions of at least one other of the plurality of filars.

In Example 19, the temporary implantable medical device lead according to either Example 17 or Example 18, and further comprising a conductive mechanical element including one or more grooves that electrically couple with the uninsulated portion of at least one filar.

In Example 20, the temporary implantable medical device lead according to Example 19, wherein one or more grooves have a depth approximately equal to a diameter of the retained at least one filar.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
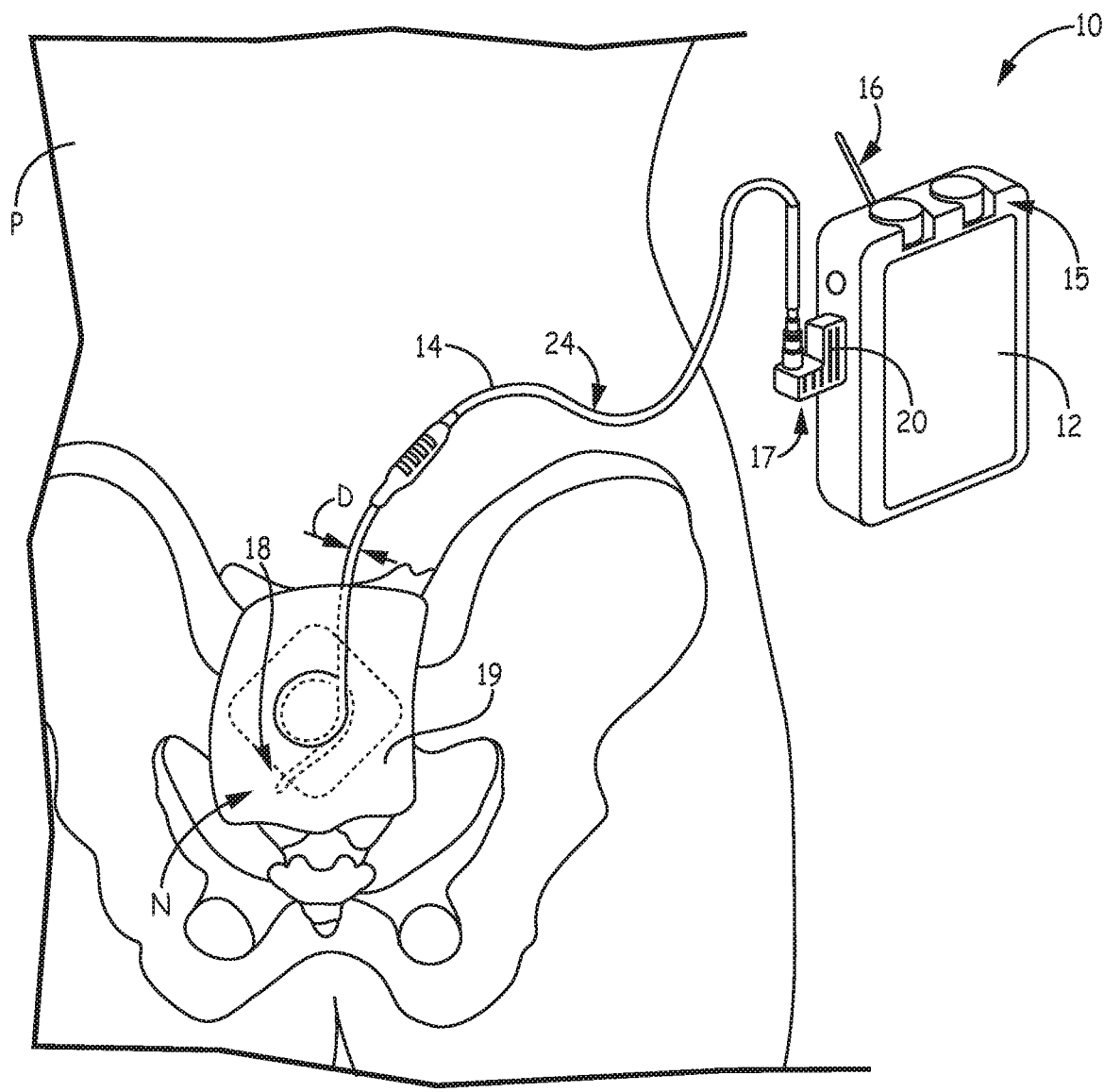
FIG. 1 illustrates an embodiment of a multipolar temporary lead positioned proximate the sacral nerves of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an embodiment of an electrical stimulation system 10 including a control module (e.g., stimulator or pulse generator) 12 and a temporary implantable medical device lead 14 coupled to the control module 12. In some embodiments, the electrical stimulation system 10 is a peripheral nerve evaluation (PNE) stimulation system, which allows temporary implantation of a lead at a nerve site to test whether neurostimulation at the site improves the condition being treated. In the embodiment shown, the lead 14 is implanted proximate a sacral nerve N of a patient P. In other embodiments, the electrical stimulation system 10 is configured to provide stimulation to other nerve bundles or other portions or systems of the body. While illustrated and described as a temporary lead, the lead 14 may alternatively be configured as a chronically implanted lead.

The control module 12 is configured to deliver stimulation signals to the lead 14 and/or receive electrical signals sensed by the lead 14. In some embodiments, the control module 12 is an externally carried or worn device. The control module 12 may include external controls 15 that allow the clinician to set characteristics (e.g., periodicity, frequency, amplitude, etc.) of the therapy delivered to the sacral nerve N via the lead 14. The control module 12 may also include an antenna 16 configured to communicate with an external device (e.g., programmer), for example to receive programming related to therapy delivery.

The lead 14 includes a proximal end 17 and a distal end 18. In some embodiments, the distal end 18 of the lead 14 includes a plurality of electrodes (not shown) positioned proximate to the sacral nerve N. The lead 14 may be introduced from the posterior side of the sacrum, through a foramen thereof, and into the region of the sacral nerves and positioned such that a plurality of electrodes at the distal end 18 is in close vicinity to the sacral nerve N for electrical stimulation. At the percutaneous entry site on the back of the patient P, the lead 14 may be coiled and affixed to the skin with a transparent dressing 19. At the proximal end 17, the lead includes a connector 20 configured to mechanically and electrically couple the lead 14 to the control module 12. The connector 20 may include a plurality of contacts that electrically couple the electrodes at the distal end 18 of the lead 14 to the electrical components of the control module 12 via a conductor extending through the lead 14.

The conductor extending through the lead 14 is a helically coiled multifilar conductor. As used herein, a filar may be a single conductive wire or a cable comprising a plurality of bundled wires. The multifilar conductor is electrically connected to the control module 12 such that different wires of the conductor are capable of carrying different electrical signals for stimulation of the sacral nerve N. In some embodiments, the multifilar conductor is electrically insulated with a layer of insulating material that surrounds each filar. According to embodiments of the present disclosure, and as will be more fully described herein, the insulative layer is removed from an uninsulated portion of each of the filars near the distal end 18. The uninsulated portion of each of the filars is exposed at an exterior of the body of the lead 14 such that the exposed uninsulated portions of the filars define the plurality of electrodes at longitudinally spaced sections along a distal region near the distal end of the lead 14.

With a plurality of electrodes, the lead 14 according to the present disclosure is configured for multipolar stimulation, thereby eliminating the ground pad used in unipolar PNE systems. In addition, the multiple electrodes at the distal end 18 of the lead 14 improves the likelihood that therapeutic stimulation of the sacral nerve N is consistently delivered during the evaluation period, due to the number of electrodes disposed in proximity to the sacral nerve N. That is, even if the lead 14 migrates during the evaluation period and one of the electrodes at the distal end 18 moves away from the sacral nerve N, other electrodes at the distal end 18 may come into contact with the sacral nerve N after the migration.

In some embodiments, the lead 14 has a relatively small outer diameter D. In some embodiments, the outer diameter D is less than about 0.05 inch (1.27 mm). For example, in some embodiments, the outer diameter is less than about 0.025 inch (0.635 mm). The outer diameter D may be such that the lead 14 can be implanted using a small diameter needle having a lumen diameter corresponding to the outer diameter D. For example, in some embodiments, the needle used for implantation of the lead 14 may be a 16 gauge or 20 gauge foramen needle.

In some embodiments, the outer surface of the lead 14 is defined by the insulated and uninsulated filars of the lead conductor. In alternative embodiments, the lead 14 may include a lead body 24 that covers the lead conductor. Portions of the lead body 24 at the location of uninsulated portions of the lead conductor at the distal end 18 may be removed to expose the electrodes at an exterior of the lead body 24. In some embodiments, the lead body 24 is comprised of an insulative material, such as, for example, ethylene tetrafluoroethylene (ETFE), polytetrafluoroethylene (PTFE), parylene, other fluoropolymers, silicone, polyurethane, polyester, or rubber. In alternative embodiments, the lead 14 does not include an insulative lead body 24.

Figure 2:
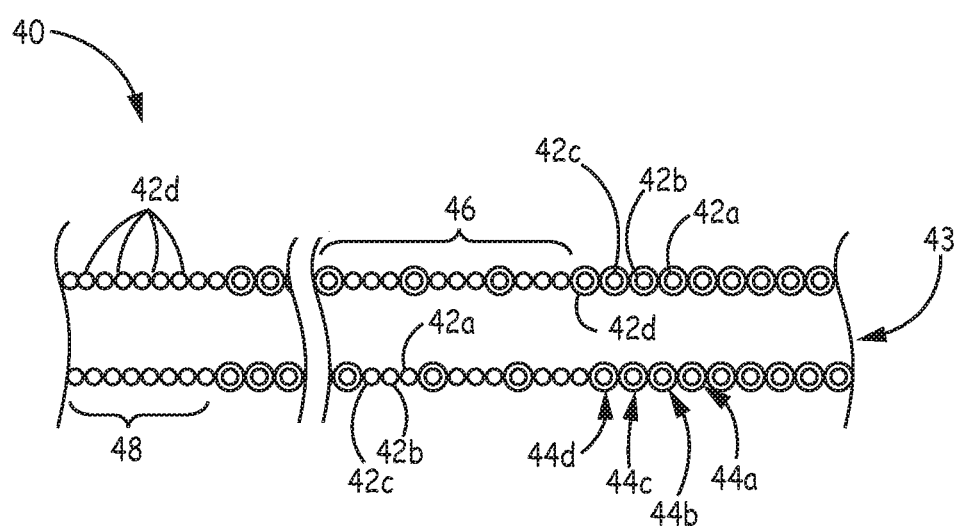
FIG. 2 is a cross-sectional view of an embodiment of a temporary lead coil conductor including a multifilar conductor having insulative coating removed to form a plurality of electrodes.

FIG. 2 is a cross-sectional view of an embodiment of a multifilar temporary lead coil conductor 40 according to the present disclosure. The portion of the lead conductor 40 illustrated in FIG. 2 is near the distal end 18 of the lead 14, and does not illustrate the distal tip of the lead 14 or the portions of the lead proximal to the electrodes. In the embodiment shown, the conductor 40 includes four filars 42a, 42b, 42c, and 42d. While four filars 42a-42d are shown, any number of filars 42 is possible. For example, in other embodiments, the conductor 40 includes two to eight filars. The filars 42a-42d may be comprised of a conductive material such as, for example, stainless steel, MP35N, platinum, platinum-iridium, or tantalum.

The filars 42a-42d are wound co-radially with each other such that the filars 42a-42d define a helically wound coil including an inner lumen 43. In some embodiments, the inner lumen 43 has a diameter of less than about 0.015 inch (0.381 mm), and is configured to allow passage of a stylet for delivery of the lead 14 to the implantation site.

The filars 42a-42d are each coated circumferentially with an insulative material 44a, 44b, 44c, and 44d, respectively. The insulative material 44a-44d electrically isolates the filars 42a-42d from each other. In some embodiments, the insulative material 44a-44d is comprised of a material such as, for example, ETFE, PTFE, parylene, silicone, or polyurethane, although other insulative materials are also possible. In some embodiments, the insulative material 44a-44d on each of the filars 42a-42d is comprised of the same insulative material. In alternative embodiments, the insulative material 44a-44d differs between some of the filars 42a-42d.

The diameter of each of the filars 42a-42d may be less than about 0.006 inch (0.152 mm), and a thickness of the insulative material 44a-44d may be less than about 0.002 inch (0.051 mm). In some embodiments, the thickness of the insulative material 44a-44d is in the range of about 0.00025 inch to about 0.001 inch (0.006-0.025 mm). The filars 42a-42d are closely wound such that the spacing between adjacent turns of the conductor 40 is less than about 0.005 inch (0.127 mm). In some embodiments, the spacing between adjacent turns of the conductor 40 is less than about 0.001 inch (0.025 mm).

In various embodiments, the insulative layer 44a-44d is removed from sections of the filars 42a-42d near the distal end 18 of the lead 14 to define a plurality of longitudinally spaced electrodes. For example, the insulative layer 44a-44d may be removed from sections of the filars 42a-42d via an ablation process. In the embodiment shown, the insulative layer 44a-44c is removed from the filars 42a-42c, respectively, to expose the conductive material of the filars 42a-42c at an exterior of the lead 14. The uninsulated portions of the filars 42a-42c define an electrode 46. Also in the embodiment shown, the insulative layer 44d is removed from the filar 42d to expose the conductive material of the filar 42d at an exterior of the lead 14 and define an electrode 48. The electrode 48 is located distally from the electrode 46. While electrodes 46, 48 are illustrated as extending co-radially with the insulated portions of the filars 42a-42d, in some embodiments, the electrodes 46, 48 are disposed at the outer surface of the conductor 40 to form a substantially constant outer diameter. That is, in some embodiments, the outer diameter of the insulated filars 42a-42d is approximately equal to the outer diameters of the electrodes 46, 48. In still further embodiments, the outer diameters of the electrodes 46 and/or 48 are greater than the outer diameter of the insulated filars 42a-42d.

In some embodiments, the filars 42a-42c terminate proximal to the electrode 48 such that turns of the filar 42d are adjacent to each other at the electrode 48. Alternatively, the filars 42a-42c may extend distal to the electrode 48 in insulated form. While the electrode 46 is shown defined by three filars 42a-42c and the electrode 48 is shown defined by one filar 42d, the electrodes 46 and 48 can alternatively be defined by any number of filars 42 in the conductor 40 (e.g., two filars define electrode 46 and two filars define electrode 48). In some embodiments, the turns of the uninsulated portions of the filars 42a-42c that define electrode 46 and/or the uninsulated portion of the filar 42d that defines electrode 48 are welded together. In some embodiments, the longitudinal lengths of the electrodes 46, 48 are less than about 0.500 inch (12.7 mm). For example, the electrodes 46, 48 may be approximately 0.100 inch (2.54 mm) in length. In some embodiments, the electrodes 46, 48 are disposed on the distal one inch (25.4 mm) of the lead 14.

Figure 3A:
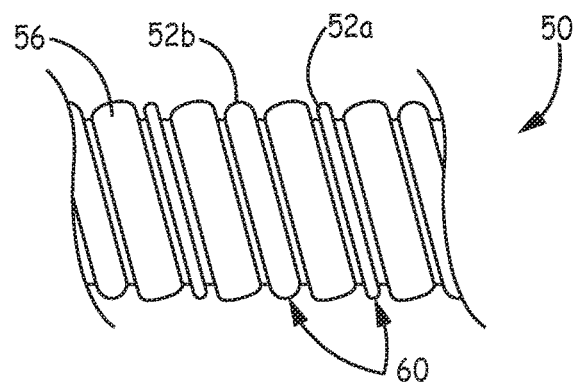
FIG. 3A is a side view of an embodiment of a temporary lead coil conductor including a mechanical element disposed within turns of the coil conductor to define an electrode.
Figure 3B:
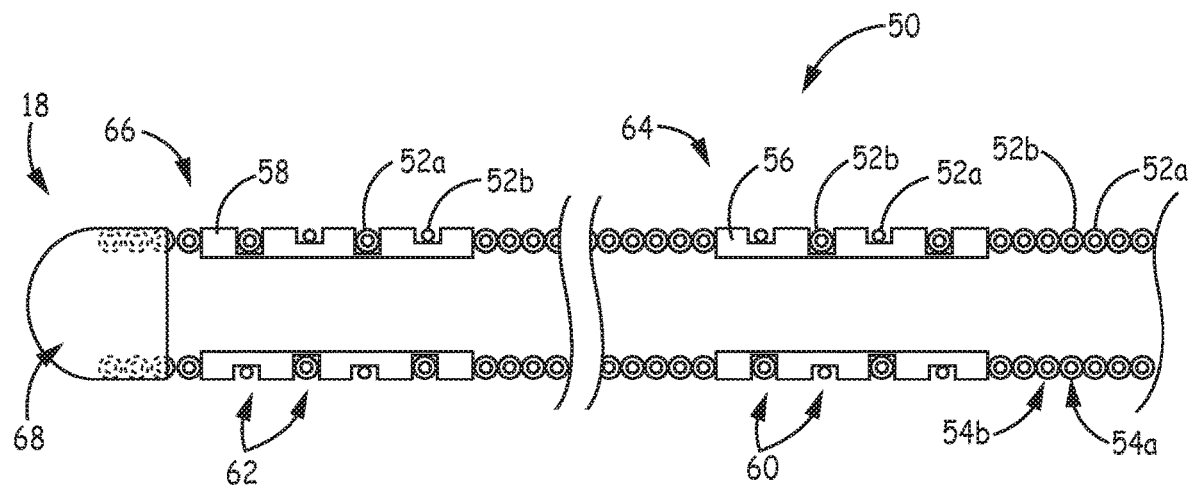
FIG. 3B is a cross-sectional view of the temporary lead coil conductor illustrated in FIG. 3A.

FIG. 3A is a side view, and FIG. 3B is a cross-sectional view, of a portion of a temporary lead coil conductor 50 according to another embodiment of the present disclosure. In the illustrated embodiment, the conductor 50 is a bifilar conductor including filars 52a and 52b coated by insulative layers 54a and 54b, respectively. The filars 52a and 52b may be comprised of a conductive material such as those discussed herein with respect to filars 42a-42d. The insulative layers 54a and 54b may be comprised of an insulative material such as those discussed herein with respect to insulative layers 44a-44d. In addition, the dimensions of the filars 52a and 52b and insulative layers 54a and 54b may be similar to the dimensions of filars 42a-42d and insulative layers 44a-44d as described herein. While the conductor 50 includes two filars 52a and 52b, the conductor 50 may alternatively include more than two filars.

The conductor 50 includes proximal mechanical element 56 and distal mechanical element 58. In some embodiments, the mechanical elements 56 and 58 are solid machined elements comprising a conductive material, such as, for example, stainless steel, MP35N, platinum, platinum-iridium, or tantalum, although other conductive materials are also possible. The mechanical elements 56 and 58 are configured to receive turns of the filars 52a and 52b and retain the filars 52a and 52b at an exterior of the lead 14. In some embodiments, the mechanical element 56 includes longitudinally spaced grooves 60 and the mechanical element 58 includes longitudinally spaced grooves 62 sized and shaped to receive turns of the filars 52a and 52b. FIG. 3A illustrates a side view of the portion of the conductor 50 including the proximal mechanical element 56.

In the embodiment shown, the insulative layer 54a is removed (e.g., via ablation) from the filar 52a along the portion of the filar 52a retained by the proximal mechanical element 56, and the insulative layer 54b is removed from the filar 52b along the portion of the filar 52b retained by the distal mechanical element 58. The uninsulated portion of the filar 52a and the mechanical element 56 define a proximal electrode 64 and the uninsulated portion of the filar 52b and the mechanical element 58 define a distal electrode 68. In some embodiments, the uninsulated portions of filars 52a, 52b are connected to the mechanical elements 56, 58 by, for example, laser welding in one or more locations or along the entire length of the mechanical elements 56, 58.

In some embodiments, the depths of the grooves 60, 62 in the mechanical elements 56, 58 are such that the grooves 60, 62 that retain the uninsulated portions of the filars 52a, 52b are not as deep as the grooves 60, 62 that retain the portions of the filars 52a, 52b including the insulative layers 54a, 54b. For example, the depth of the grooves 60, 62 that retain the uninsulated portions of the filar 52a, 52b may be approximately equal to the diameter of the uninsulated filars 52a, 52b, and the depth of the grooves 60, 62 that retain the insulated portions of the filar 52a, 52b may be approximately equal to the diameter of the insulated filars 52a, 52b. In this configuration, the exterior surface of the lead 14 remains substantially uniform, while positioning the uninsulated portions of the filars 52a, 52b at the exterior surface of the lead 14. In alternative embodiments, the electrodes 66, 68 have a greater outer diameter than the outer diameter of the insulated filars 52a, 52b.

The lead 14 may optionally include a tip cover 68 at a distal end 18. The tip cover 68 may be molded or bonded onto the distal end 18 and facilitates easy traversal of the lead 14 to the implantation site. Alternatively, the tip cover 68 is comprised of a conductive material such that the tip cover 68 is operable as a distal electrode.

Figure 4:
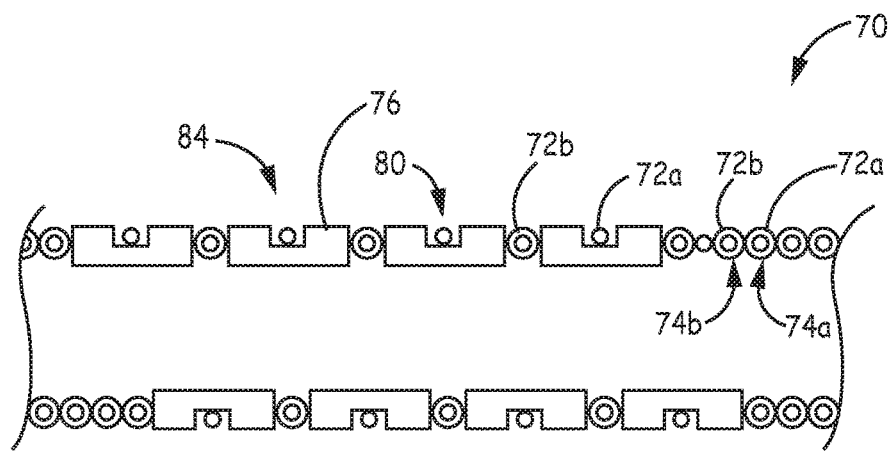
FIG. 4 is a cross-sectional view of an embodiment of a temporary lead coil conductor including a contoured ribbon formed among turns of the coil conductor to define an electrode.

FIG. 4 is a cross-sectional view of a temporary lead coil conductor 70 according to another embodiment of the present disclosure. In the illustrated embodiment, the conductor 70 is a bifilar conductor including filars 72a and 72b coated by insulative layers 74a and 74b, respectively. The filars 72a and 72b may be comprised of a conductive material such as those discussed herein with respect to filars 42a-42d. The insulative layers 74a and 74b may be comprised of an insulative material such as those discussed herein with respect to insulative layers 44a-44d. In addition, the dimensions of the filars 72a and 72b and insulative layers 74a and 74b may be similar to the dimensions of filars 42a-42d and insulative layers 44a-44d as described herein. While the conductor 70 includes two filars 72a and 72b, the conductor 70 may alternatively include more than two filars.

The conductor 70 is a variation on the conductor 50 illustrated in FIGS. 3A and 3B, wherein instead of solid elements defining the electrode structure, the electrode structure is defined by a mechanical element 76 comprising a contoured conductive ribbon structure. In this arrangement, the uninsulated portions of the filar defining the electrode (e.g., filar 72a in FIG. 4) are retained in a groove 80 defined in the mechanical element 76, and the insulated filar (e.g., filar 72b in FIG. 4) is alternatingly wound between turns of the mechanical element 76. The uninsulated portions of the filar 72a and the electrically coupled mechanical element 76 define an electrode 84 on the lead 14. Similar mechanical elements may be formed at other longitudinally spaced sections of the lead 14 to define additional electrodes.

Figure 5:
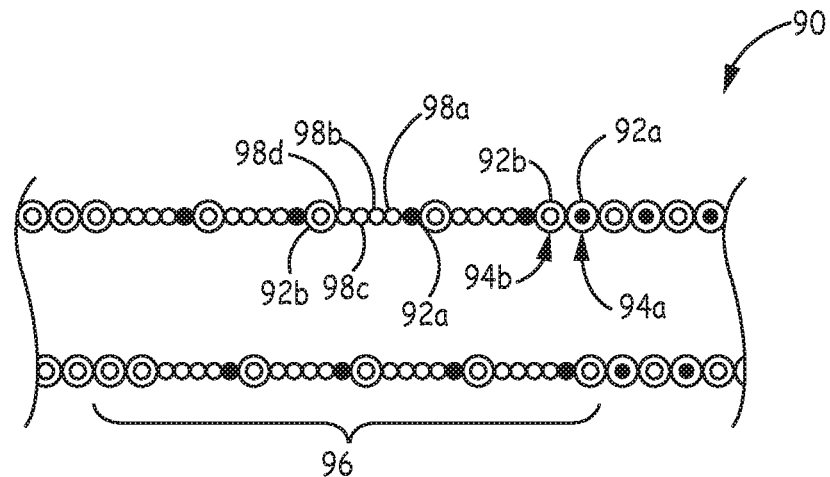
FIG. 5 is a cross-sectional view of an embodiment of a temporary lead coil conductor including one or more additional filars wound with turns of the coil conductor to define an electrode.

FIG. 5 is a cross-sectional view of a temporary lead coil conductor 90 according to another embodiment of the present disclosure. In the illustrated embodiment, the conductor 90 is a bifilar conductor including filars 92a and 92b coated by insulative layers 94a and 94b, respectively. The filars 92a and 92b may be comprised of a conductive material such as those discussed herein with respect to filars 42a-42d. The insulative layers 94a and 94b may be comprised of an insulative material such as those discussed herein with respect to insulative layers 44a-44d. In addition, the dimensions of the filars 92a and 92b and insulative layers 94a and 94b may be similar to the dimensions of filars 42a-42d and insulative layers 44a-44d as described herein. While the conductor 90 includes two filars 92a and 92b, the conductor 90 may alternatively include more than two filars.

The insulative layer 94a is removed from the filar 92a along a portion of the conductor 90 to provide an electrode 96. In order to increase the surface area of the conductive portions of the electrode 96, the conductor 90 further includes additional uninsulated filars 98a, 98b, 98c, 98d wound adjacent to the uninsulated portion of the filar 92a. The filars 98a-98d are not connected to the connector 20 at the proximal end 17 of the lead 14, and thus do not receive electrical signals directly from the control module 12. Rather, the filars 98a-98d conduct the electrical signals received by the filar 92a from the control module 12. In some embodiments, the terminal ends of the filars 98a-98d are at or near the proximal and distal ends of the electrode 96. The filars 98a-98d may be comprised of a conductive material similar to filars 42a-42d as discussed herein. In some embodiments, the filars 98a-98d are electrically and mechanically coupled to the uncoated filar 92a via laser welding. While four additional filars 98a-98d are shown, the conductor 90 may include any number of filars 98 to increase the surface area of the electrode 96. Similar assemblies of additional filars adjacent to uninsulated portions of filars 92 may be formed at other longitudinally spaced sections of the lead 14 to define additional electrodes. While electrode 96 is illustrated as extending co-radially with the insulated portions of the filars 92a and 92b, in some embodiments, the electrode 96 is disposed at the outer surface of the conductor 90 to form a substantially constant outer diameter. That is, in some embodiments, the outer diameter of the insulated filars 92a, 92b is approximately equal to the outer diameter of the electrode 96. In still further embodiments, the outer diameter of the electrode 96 is greater than the outer diameter of the insulated filars 92a, 92b.

Figure 6:
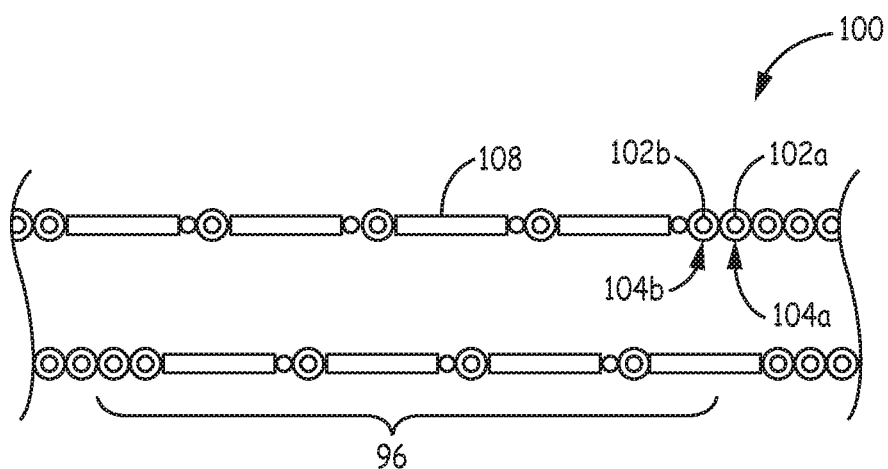
FIG. 6 is a cross-sectional view of an embodiment of a temporary lead coil conductor including a conductive ribbon wound with turns of the coil conductor to define an electrode.

FIG. 6 is a cross-sectional view of a temporary lead coil conductor 100 according to another embodiment of the present disclosure. In the illustrated embodiment, the conductor 100 is a bifilar conductor including filars 102a and 102b coated by insulative layers 104a and 104b, respectively. The filars 102a and 102b may be comprised of a conductive material such as those discussed herein with respect to filars 42a-42d. The insulative layers 104a and 104b may be comprised of an insulative material such as those discussed herein with respect to insulative layers 44a-44d. In addition, the dimensions of the filars 102a and 102b and insulative layers 104a and 104b may be similar to the dimensions of filars 42a-42d and insulative layers 44a-44d as described herein. While the conductor 100 includes two filars 102a and 102b, the conductor 100 may alternatively include more than two filars.

The conductor 100 is a variation on the conductor 90 illustrated in FIG. 5, wherein instead of additional filars employed to increase the surface area of the electrode, the electrode 106 in the conductor 100 includes a conductive ribbon 108 to increase the electrode surface area. That is, the insulative layer 104a is removed from the filar 102a along a portion of the conductor 100. The conductive ribbon 108 is wound adjacent to the uninsulated portion of the filar 102a. The conductive ribbon 108 is not connected to the connector 20 at the proximal end 17 of the lead 14, and thus does not receive electrical signals directly from the control module 12. Rather, the conductive ribbon 108 conducts the electrical signals received by the filar 102a from the control module 12. In some embodiments, the conductive ribbon 108 is welded to the uninsulated portions of the filar 102a. The conductive ribbon 108 may be comprised of a conductive material similar to filars 42a-42d as discussed herein. While electrode 106 is illustrated as extending co-radially with the insulated portions of the filars 102a and 102b, in some embodiments, the electrode 106 is disposed at the outer surface of the conductor 100 to form a substantially constant outer diameter. That is, in some embodiments, the outer diameter of the insulated filars 102a, 102b is approximately equal to the outer diameter of the electrode 106. In still further embodiments, the outer diameter of the electrode 106 is greater than the outer diameter of the insulated filars 102a, 102b.

Figure 7:
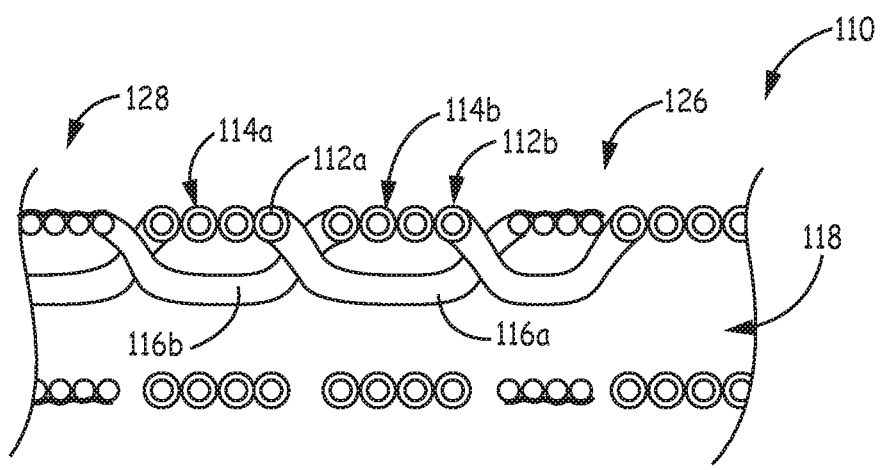
FIG. 7 is a cross-sectional view of an embodiment of a temporary lead coil conductor including a plurality of filars wound in alternating multi-turn segments.

FIG. 7 is a cross-sectional view of a temporary lead coil conductor 110 according to another embodiment of the present invention. In the illustrated embodiment, the conductor 110 is a bifilar conductor including filars 112a and 112b coated by insulative layers 114a and 114b, respectively. The filars 112a and 112b may be comprised of a conductive material such as those discussed herein with respect to filars 42a-42d. The insulative layers 114a and 114b may be comprised of an insulative material such as those discussed herein with respect to insulative layers 44a-44d. In addition, the dimensions of the filars 112a and 112b and insulative layers 114a and 114b may be similar to the dimensions of filars 42a-42d and insulative layers 44a-44d as described herein. While the conductor 110 includes two filars 112a and 112b, the conductor 110 may alternatively include more than two filars.

The filars 112a and 112b of the conductor 110 are wound in alternating multi-turn segments. In the embodiment shown, the filars 112a, 112b are wound in alternating four turn segments. To achieve this configuration, the filar 112a is wound with a plurality of adjacent turns, and then a connecting portion 116a extends within the lumen 118 formed by turns of the filar 112b to the next multi-turn segment of the filar 112a. Likewise, the filar 112b is wound with a plurality of adjacent turns, and then a connecting portion 116b extends within the lumen 118 formed by turns of the filar 112a to the next multi-turn segment of the filar 112b.

To form electrodes, the insulative layer 114a, 114b is removed from one or more multi-turn segments of the filars 112a, 112b. For example, in the embodiment illustrated in FIG. 7, the insulative layer 114a is removed from a multi-turn segment of the filar 112a to form a proximal electrode 126, and the insulative layer 114b is removed from a multi-turn segment of the filar 112b to form a distal electrode 128. In some embodiments, the uninsulated multi-turn segment of the filar 112a forming the electrode 126 are welded together, and/or the uninsulated multi-turn segment of the filar 112b forming the electrode 128 are welded together. The welding forms an electrode surface at an exterior of the lead 14.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A temporary implantable medical device lead comprising:
    a connector configured to connect the lead to an external control module;
    a helically coiled conductor having a proximal end mechanically and electrically connected to the connector, the conductor including a plurality of filars mechanically and electrically connected to the connector; and
    a first mechanical element comprising a metal tube having a plurality of longitudinally spaced grooves formed along an exterior of the tube,
    wherein the plurality of longitudinally spaced grooves receive at least some of the plurality of filars, the at least some of the plurality of filars electrically connected to the first mechanical element such that the first mechanical element is configured as an electrode to deliver electrical stimulation to portions or systems of a body from the external control module.

2. The temporary implantable medical device lead of claim 1, further comprising a second mechanical element comprising a metal tube having at least one groove formed along an exterior of the tube, wherein at least one of the plurality of filars is received by the at least one groove, the at least one of the plurality of filars is electrically connected to the second mechanical element such that the second mechanical element is configured as an electrode to deliver electrical stimulation to portions or systems of a body from the external control module, and the second mechanical element is distal of the first mechanical element.

3. The temporary implantable medical device lead of claim 1, wherein the plurality of longitudinally spaced grooves comprise a first set of one or more grooves and a second set of one or more grooves, the first set of one or more grooves receives at least one of the plurality of filars, and the second set of one or more grooves receives at least one other of the plurality of filars, the second set of one or more grooves being deeper than the first set of one or more grooves.

4. The temporary implantable medical device lead of claim 3, wherein the first set of one or more grooves have a depth approximately equal to a diameter of the received at least one of the plurality of filars.

5. The temporary implantable medical device lead of claim 3, wherein the first set of one or more grooves have a depth approximately greater than a diameter of the received at least one of the plurality of filars.

6. The temporary implantable medical device lead of claim 1, wherein the plurality of filars are electrically insulated from the connector to the first mechanical element.

7. The temporary implantable medical device lead of claim 1, wherein the plurality of filars are uninsulated and exposed along the first mechanical element.

8. The temporary implantable medical device lead of claim 1, wherein the plurality of filars are welded to the first mechanical element.

9. The temporary implantable medical device lead of claim 1, further including a tip cover at least one of bonded and molded to a distal end of the lead.

10. The temporary implantable medical device lead of claim 9, wherein the tip cover is comprised of a conductive material such that the tip cover is operable as a tip electrode.

11. A system comprising:
an externally carried control module; and
a temporary implantable medical device lead including:
 a connector configured to connect the lead to the control module;
 a helically coiled conductor having a proximal end mechanically and electrically connected to the connector, the conductor including a plurality of filars mechanically and electrically connected to the connector; and
 a first mechanical element comprising a metal tube having a plurality of longitudinally spaced grooves formed along an exterior of the tube,
 wherein the plurality of longitudinally spaced grooves receive at least some of the plurality of filars, the at least some of the plurality of filars electrically connected to the first mechanical element such that the first mechanical element is configured as an electrode to deliver electrical stimulation to portions or systems of a body from the control module.

12. The system of claim 11, further comprising a second mechanical element comprising a metal tube having at least one groove formed along an exterior of the tube, wherein at least one of the plurality of filars is received by the at least one groove, the at least one of the plurality of filars is electrically connected to the second mechanical element such that the second mechanical element is configured as an electrode to deliver electrical stimulation to portions or systems of a body from the control module, and the second mechanical element is distal of the first mechanical element.

13. The system of claim 11, wherein the plurality of longitudinally spaced grooves comprise a first set of one or more grooves and a second set of one or more grooves, the first set of one or more grooves receives at least one of the plurality of filars, and the second set of one or more grooves receives at least one other of the plurality of filars, the second set of one or more grooves being deeper than the first set of one or more grooves.

14. The system of claim 13, wherein the first set of one or more grooves have a depth approximately equal to a diameter of the received at least one of the plurality of filars.

15. The system of claim 13, wherein the first set of one or more grooves have a depth approximately greater than a diameter of the received at least one of the plurality of filars.

16. The system of claim 11, wherein the plurality of filars are electrically insulated from the connector to the first mechanical element.

17. The system of claim 11, wherein the plurality of filars are uninsulated and exposed along the first mechanical element.

18. The system of claim 11, wherein the plurality of filars are welded to the first mechanical element.

19. The system of claim 11, further including a tip cover at least one of bonded and molded to a distal end of the lead.

20. The system of claim 19, wherein the tip cover is comprised of a conductive material such that the tip cover is operable as a tip electrode.

* * * * *